United States Patent
Alden et al.

(10) Patent No.: US 11,604,123 B2
(45) Date of Patent: Mar. 14, 2023

(54) SOLID PHASE EXTRACTION METHODS FOR ENHANCED REMOVAL OF PHOSPHOLIPIDS FROM BIOLOGICAL SAMPLES

(71) Applicant: WATERS TECHNOLOGIES CORPORATION, Milford, MA (US)

(72) Inventors: Bonnie A. Alden, Whitinsville, MA (US); Kenneth Berthelette, Millville, MA (US); Jon Finch, Plymouth, MI (US); Donna Osterman, Northbridge, MA (US); Thomas Swann, Hopedale, MA (US); Thomas H. Walter, Ashland, MA (US)

(73) Assignee: Waters Technologies Corporation, Milford, MA (US)

( * ) Notice: Subject to any disclaimer, the term of this patent is extended or adjusted under 35 U.S.C. 154(b) by 483 days.

(21) Appl. No.: 16/230,567

(22) Filed: Dec. 21, 2018

(65) Prior Publication Data
US 2019/0195758 A1    Jun. 27, 2019

Related U.S. Application Data

(60) Provisional application No. 62/609,262, filed on Dec. 21, 2017.

(51) Int. Cl.
*G01N 1/40* (2006.01)
*B01D 15/38* (2006.01)
(Continued)

(52) U.S. Cl.
CPC ........... *G01N 1/405* (2013.01); *B01D 15/327* (2013.01); *B01D 15/362* (2013.01);
(Continued)

(58) Field of Classification Search
CPC ............ G01N 2030/009; G01N 1/405; G01N 2405/00; G01N 33/92; G01N 2030/062;
(Continued)

(56) References Cited

U.S. PATENT DOCUMENTS 7,232,520 B1   6/2007  Lee et al.
7,442,299 B2   10/2008 Lee et al.
(Continued)

OTHER PUBLICATIONS

Chambers, E., et al., Systematic and comprehensive strategy for reducing matrix effects in LC/MS/MS analyses, J. Chromatogr. B 852:22-34 (2007).
(Continued)

*Primary Examiner* — Rebecca M Fritchman
(74) *Attorney, Agent, or Firm* — Womble Bond Dickinson (US) LLP; Deborah M. Vernon; Dennis Parad

(57) ABSTRACT

In various aspects, the present disclosure pertains to methods of performing a sample enrichment procedure, which comprise: adding a sample fluid that comprises at least one phospholipid and at least one target analyte to a sorbent that comprises a hydrophobic component and a cation exchange component, thereby resulting in sorbent with bound phospholipid and bound target analyte; adding an aqueous solution comprising an acidic compound and a salt; adding an organic solution to the sorbent thereby desorbing at least a portion of the bound phospholipid from the sorbent; and adding an elution solution to the sorbent, thereby desorbing at least a portion of the bound target analyte from the sorbent and forming a solution of the target analyte in the elution solution. In other aspects, the present disclosure pertains to kits, which may be used in conjunction with such methods.

20 Claims, 3 Drawing Sheets

(51) Int. Cl.
*B01D 15/42* (2006.01)
*B01D 15/36* (2006.01)
*B01J 39/26* (2006.01)
*B01J 39/05* (2017.01)
*B01D 15/32* (2006.01)
*G01N 33/92* (2006.01)
*G01N 30/06* (2006.01)
*G01N 30/00* (2006.01)

(52) U.S. Cl.
CPC ....... *B01D 15/3847* (2013.01); *B01D 15/426* (2013.01); *B01J 39/05* (2017.01); *B01J 39/26* (2013.01); *G01N 33/92* (2013.01); *G01N 2030/009* (2013.01); *G01N 2030/062* (2013.01); *G01N 2405/00* (2013.01)

(58) Field of Classification Search
CPC .. B01D 15/362; B01D 15/426; B01D 15/327; B01D 15/3847; B01J 39/26; B01J 39/05
See application file for complete search history.

(56) References Cited

U.S. PATENT DOCUMENTS

| | | | | |
|---|---|---|---|---|
| 2010/0285596 | A1* | 11/2010 | Yu | G01N 1/4055 436/71 |
| 2014/0194283 | A1* | 7/2014 | Jiang | B01J 20/265 521/154 |
| 2015/0346170 | A1* | 12/2015 | Huang | H01J 49/0031 436/500 |
| 2019/0324043 | A1* | 10/2019 | Wuttke | B01L 3/502753 |

OTHER PUBLICATIONS

Neville, D., et al., "Efficacy of plasma phospholipid removal during sample preparation and subsequent retention under typical UHPLC conditions" Bioanalysis 4(7):795-807 (2012).

Huq, S.W., et al., Automated SPE Method Development Using Strata™—X 96-Well SPE Method Development Plates in Conjunction with a Tecan Freedom EVO Liquid Handling System, TN-0078 Applications Phenomenex®, Inc. (2015) 8 pages.

Evolute® Express User Guide for Load-Wash-Elute SPE, Part No. UI330, Biotage® (2016) 36 pages.

Waters Oasis Carridges and 96-Well Plates—Care and User Guide, Waters Corporation (2017) 13 pages.

International Search Report and Written Opinion for International application No. PCT/US2018/067293, dated Mar. 15, 2019, 11 pages.

Ismaiel, O.A., et al., "Investigation of endogenous blood plasma phospholipids, cholesterol and glycerides that contribute to matrix effects in bioanalysis by liquid chromatography/mass spectrometry", Journal of Chromatography B: Biomedical Sciences & Applications 878(31):3303-3316 (2010).

Author unknown, "Waters Oasis Sample Extraction SPE Products", Waters [online] 2020 [retrieved on Jun. 15, 2020]. Retrieved from Internet URL: https://web.archive.org/web/20171106163314/http:/www.waters.com:80/waters/en_US/Waters-Oasis-Sample-Extraction-SPE-Products/nav.htm?cid=513209&locale=en_US, Nov. 6, 2017, 5 pages.

* cited by examiner

SOLID PHASE EXTRACTION METHODS FOR ENHANCED REMOVAL OF PHOSPHOLIPIDS FROM BIOLOGICAL SAMPLES

CROSS REFERENCE TO RELATED APPLICATION

This application claims the benefit of U.S. Provisional Application No. 62/609,262, filed Dec. 21, 2017 and entitled "SOLID PHASE EXTRACTION METHODS FOR ENHANCED REMOVAL OF PHOSPHOLIPIDS FROM BIOLOGICAL SAMPLES", which is hereby incorporated by reference.

BACKGROUND

The present disclosure relates to methods and kits for the enhanced removal of phospholipids from biological samples by Solid Phase Extraction (SPE). Biological samples frequently contain phospholipids which can interfere with sample analyses, including liquid chromatography-mass spectrometry (LC-MS) analysis, commonly resulting in signal suppression or enhancement. Phospholipids may also lead to column and instrument fouling during LC-MS analysis. Removing phospholipids is beneficial to improve signal-to-noise ratios and data reproducibility.

SUMMARY

In various aspects, the present disclosure pertains to methods of performing sample enrichment procedures, which comprise: adding a sample fluid that comprises at least one phospholipid and at least one target analyte to a sorbent that comprises a hydrophobic component and a cation exchange component (e.g., a sorbent comprising a copolymer that comprises a hydrophobic organic monomer, an organic monomer comprising a cation-exchange group, and optionally a hydrophilic organic monomer, among other possibilities), thereby resulting in sorbent with bound phospholipid and bound target analyte; adding an aqueous solution comprising an acidic compound and a salt (e.g., by adding the aqueous solution to the sample fluid prior to addition of the sample fluid to the sorbent and/or by adding the aqueous solution to the sorbent after addition of the sample fluid to the sorbent); adding an organic solution to the sorbent thereby desorbing at least a portion of the bound phospholipid from the sorbent; and adding an elution solution to the sorbent, thereby desorbing at least a portion of the bound target analyte from the sorbent and forming a solution of the target analyte in the elution solution.

For example, in certain embodiments, the present disclosure is directed to methods of performing sample enrichment procedures that comprise: adding a sample fluid that comprises at least one phospholipid and at least one target analyte to a sorbent comprising an organic copolymer that comprises a hydrophobic organic monomer, a hydrophilic organic monomer and an organic monomer comprising a cation-exchange group thereby yielding sorbent with adsorbed phospholipid and adsorbed target analyte; adding an aqueous solution comprising an acidic compound and a first salt species (e.g., by adding the aqueous solution to the sample fluid prior to addition of the sample fluid to the sorbent and/or by adding the aqueous solution to the sorbent after addition of the sample fluid to the sorbent); adding an organic solution comprising a first organic solvent species to the sorbent thereby desorbing at least a portion of the phospholipid from the sorbent; adding an elution solution that comprises (a) a basic compound or a second salt species (which may be the same as or different from the first salt species) and (b) a second organic solvent species (which may be the same as or different from the first organic solvent species) to the sorbent, thereby desorbing at least a portion of the target analyte from the sorbent and forming a solution of the target analyte in the elution solution.

As another example in certain embodiments, the present disclosure is directed to methods of performing a sample enrichment procedure, the method comprising: adding an aqueous solution comprising an acidic compound and a first salt species to a sample fluid that comprises at least one phospholipid and at least one target analyte, thereby forming a pretreated sample; adding the pretreated sample to a sorbent, thereby resulting in sorbent with adsorbed phospholipid and adsorbed target analyte, wherein the sorbent comprises a hydrophobic component and a cation exchange component (e.g., a sorbent comprising a copolymer that comprises a hydrophobic organic monomer, an organic monomer comprising a cation exchange group, and optionally a hydrophilic organic monomer, among other possibilities); washing the sorbent in a single washing step wherein an organic solution comprising a first organic solvent species is added to the sorbent thereby desorbing at least a portion of the phospholipid from the sorbent; and adding an elution solution that comprises (a) a basic compound or a second salt species (which may be the same as or different from the first salt species) and (h) a second organic solvent species (which may be the same as or different from the first organic solvent species) to the sorbent, thereby desorbing at least a portion of the target analyte from the sorbent and forming a solution of the target analyte in the elution solution.

In some embodiments, which can be used in conjunction with any of the above aspects and embodiments, the target analyte may be a base with a $pK_a$ of at least 5.

In some embodiments, which can be used in conjunction with any of the above aspects and embodiments, the aqueous solution may comprise the acidic compound in an amount sufficient to provide the aqueous solution with a pH that is at least two pH units below a lowest $pK_a$ of the target analyte.

In some embodiments, which can be used in conjunction with any of the above aspects and embodiments, the acidic compound may be selected from an organic acid, phosphoric acid, hydrochloric acid, or carbonic acid.

In some embodiments, which can be used in conjunction with any of the above aspects and embodiments, the solutions of the first and second salt species may comprise the salt in an amount corresponding to an ionic strength ranging from 10-250 mM.

In some embodiments, which may be used in conjunction with any of the above aspects and embodiments, the first and second salt species may be salts that dissociate into an organic acid anion or an inorganic anion and a cation selected from a Group I metal cation, a Group II metal cation, an ammonium cation, and an amine cation. The organic acid anion may be selected, for example, from formate, acetate, propionate, butyrate, oxalate, malonate, succinate, maleate, glutarate, glycolate, lactate, malate, citrate and gluconate, among others.

In some embodiments, which can be used in conjunction with any of the above aspects and embodiments, the first and second organic solvent species may be selected from methanol, ethanol, 1-propanol, 2-propanol, acetonitrile, acetone, ethyl acetate, methyl ethyl ketone, tetrahydrofuran and blends thereof.

In some embodiments, which can be used in conjunction with any of the above aspects and embodiments, the elution solution may comprise the basic compound in an amount sufficient to provide the elution solution with a pH that is at least two pH units above a highest $pK_a$ of the target analyte.

In some embodiments, which can be used in conjunction with any of the above aspects and embodiments, the sample fluid may comprise a biological sample selected from a whole blood sample, a plasma sample, a serum sample, a food sample, and a food extract sample.

In other aspects, the present disclosure pertains to kits which may be useful, for example, in conjunction with any of the above methods, the kits comprising (a) a sorbent comprising a hydrophobic moiety and a cation exchange moiety; (b) an aqueous solution comprising an acidic compound and a first salt species; and (c) optionally, one or more of the following components: (i) a first organic solution (which may be used, for example, as the organic solution in the preceding methods) that comprises a first organic solvent species, (ii) a second organic solution (which may be used, for example, as the elution solution in the preceding methods) that comprises (iia) a second organic solvent species (which may be the same as or different from the first organic solvent species) and (iib) a basic compound or a second salt species (which may be the same as or different from the first salt species), (iii) a collection plate or collection vials, (i) a cap mat, (v) calibration and reference standards, (vi) identification tagging for each component, and (vii) instructions for use.

In various aspects, the present disclosure pertains to methods of performing sample enrichment procedures, which comprise: (a) adding a sample fluid that comprises at least one phospholipid and at least one target analyte to a sorbent that comprises a hydrophobic component and a cation exchange component that comprises a counter-ion that is not hl (e.g., a sorbent comprising a copolymer that comprises a hydrophobic organic monomer, an organic monomer comprising a cation-exchange group that comprises a counter-ion that is not H$^+$, and optionally a hydrophilic organic monomer, among other possibilities), thereby resulting in sorbent with adsorbed phospholipid and adsorbed target analyte; (b) adding a first organic solution comprising a first organic solvent to remove at least a portion of the adsorbed phospholipid; and (c) adding an elution solution that comprises (i) a basic compound or a salt species and (ii) a second organic solvent species to the sorbent, wherein the second organic solvent species may be the same as or different from the first organic solvent species, thereby desorbing at least a portion of the target analyte from the sorbent and forming a solution of the target analyte in the elution solution.

In some embodiments, the cation that is not H$^+$ may be selected from a Group I metal cation (e.g., Li$^+$, Na$^+$, K$^+$, Rb$^+$, Cs$^+$, etc.), a Group II metal cation (e.g., Be$^{2+}$, Mg$^{2+}$, Cz$^{2+}$, Ba$^{2+}$, etc.), an ammonium cation, and an amine cation.

In some embodiments, which may be used in conjunction with any of the above aspects and embodiments, the cation exchange group comprises a sulfonate moiety.

In some embodiments, which may be used in conjunction with any of the above aspects and embodiments, the first and second organic solvent species are selected from methanol, ethanol, 1-propanol, 2-propanol, acetonitrile, acetone, ethyl acetate, methyl ethyl ketone, tetrahydrofuran and blends thereof.

In some embodiments, which may be used in conjunction with any of the above aspects and embodiments, the elution solution comprises the basic compound. For example, the basic compound may be provided in an amount sufficient to provide the elution solution with a pH that is at least two pH units above a highest $pK_a$ of the target analyte.

In some embodiments, which may be used in conjunction with any of the above aspects and embodiments, the elution solution comprises the salt species. In certain of these embodiments, the salt species may be one that dissociates into (a) an organic acid anion (e.g., formate, acetate, propionate, butyrate, oxalate, malonate, succinate, maleate, glutarate, glycolate, lactate, malate, citrate, gluconate, etc.) or an inorganic anion (e.g., chloride, fluoride, bromide, hydroxide, nitrate, nitrite, sulfate, phosphate, etc.) and (b) a cation selected from a Group I metal cation, a Group II metal cation, an ammonium cation, and an amine cation. In certain of these embodiments, the elution solution that comprises the salt species comprises the salt species in an amount corresponding to an ionic strength ranging from 10-250 mM.

In some embodiments, which may be used in conjunction with any of the above aspects and embodiments, the methods further comprise adding an aqueous solution to the sorbent (e.g, after adding the sample fluid and before adding the first organic solution). In some of these embodiments, the aqueous solution comprises an organic add. In some of these embodiments, the aqueous solution comprises one or more acids selected from the following: formic acid, acetic acid, propionic acid, butyric acid, oxalic acid, malonic acid, succinic acid maleic acid, glycolic acid, lactic acid, tartaric acid, malic acid, citric acid and gluconic acid, phosphoric acid, hydrochloric acid and carbonic acid.

In some embodiments, which may be used in conjunction with any of the above aspects and embodiments, the target analyte is a base with a $pK_a$ of at least 5.

In some embodiments, which may be used in conjunction with any of the above aspects and embodiments, the sample fluid comprises a biological sample selected from a whole blood sample, a plasma sample, a serum sample, a food sample, and a food extract sample.

These and numerous other aspects and embodiments will now be described in the Detailed Description and Claims to follow.

DETAILED DESCRIPTION

Figure 1:
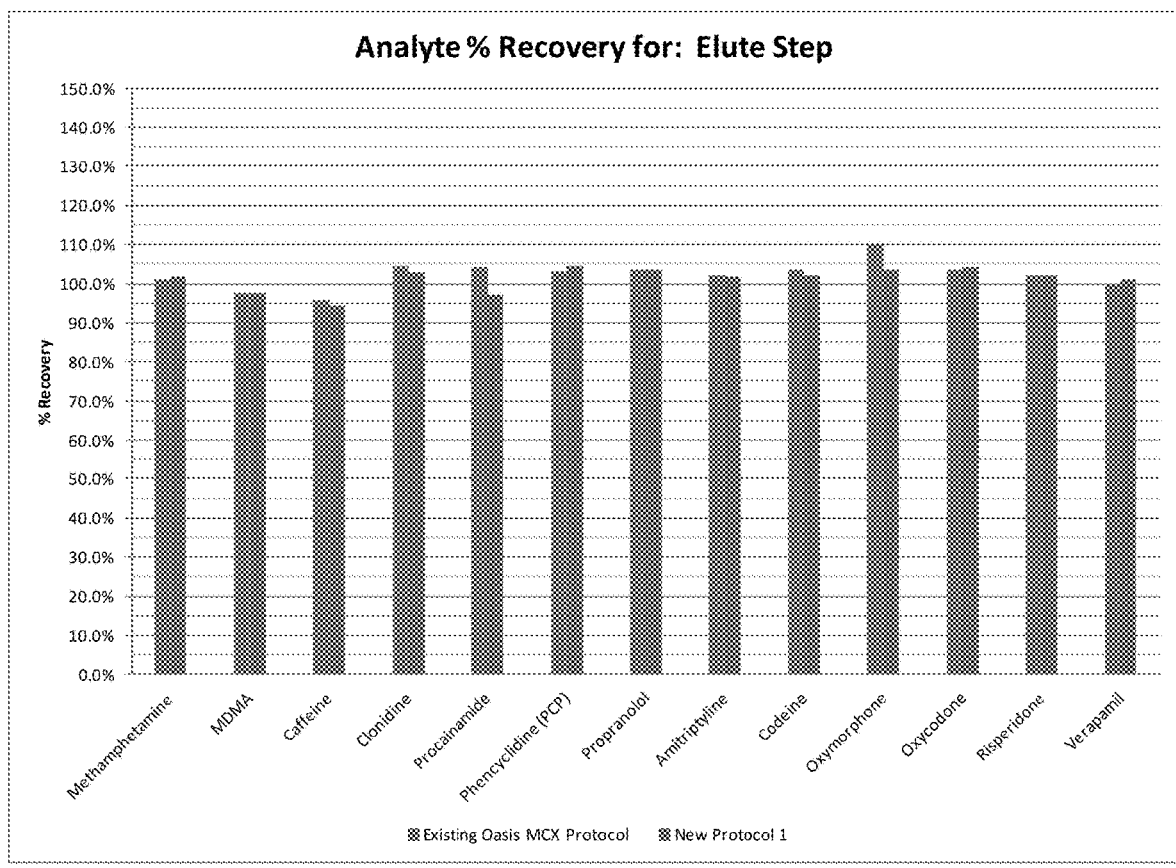
FIG. 1 shows a comparison of the elute fraction analyte % recoveries for the Existing Oasis MCX Protocol and the New Protocol 1.

The present disclosure pertains to methods for enhanced removal of phospholipids from biological samples and to sorbents, devices and kits beneficial in performing such methods.

In some aspects, the present disclosure pertains to methods of performing sample enrichment that comprise: (a) adding a sample fluid that comprises at least one phospholipid and at least one target analyte to a sorbent, wherein the sorbent comprises a hydrophobic component and a cation exchange component; (b) either (i) adding an aqueous solution comprising an acidic compound and a first salt species to the sample fluid prior to adding the sample fluid to the sorbent or (ii) adding an aqueous solution comprising an acidic compound and a salt to the sorbent after loading the sorbent with the sample fluid; (c) adding a washing solution that comprises a first organic solvent species to the sorbent thereby desorbing at least a portion of the phospholipid from the sorbent; and (d) adding an elution solution that comprises (i) a basic compound or a second salt species, which may be the same as or different from the first salt species, and (ii) a second organic solvent species, which may be the same as or different from the first organic solvent species, to the sorbent, thereby desorbing at least a portion of the target analyte from the sorbent and forming a solution of the target analyte in the elution solution. In certain of these embodiments, the cation exchange component comprises a sulfonate moiety. In certain of these embodiments, the cation exchange component comprises $H^+$ as a counter-ion.

In some aspects, the present disclosure pertains to methods of performing sample enrichment that comprise: (a) adding a sample fluid that comprises at least one phospholipid and at least one target analyte to a sorbent comprising a hydrophobic component and a cation exchange component comprising a counter-ion that is not $H^+$, thereby resulting in sorbent with adsorbed phospholipid and adsorbed target analyte; (b) adding a washing solution that comprises a first organic solvent species to remove at least a portion of the adsorbed phospholipid; and (c) adding an elution solution that comprises (i) a basic compound or a salt species and (ii) a second organic solvent species to the sorbent, wherein the second organic solvent species may be the same as or different from the first organic solvent species, thereby desorbing at least a portion of the target analyte from the sorbent and forming a solution of the target analyte in the elution solution. In certain of these embodiments, the cation exchange component comprises a sulfonate moiety. In certain of these embodiments, the counter ion that is not $H^+$ may be selected from a Group I metal cation, a Group II metal cation, an ammonium cation, and an amine cation.

In some embodiments, the target analyte is a basic target analyte having a $pK_a$ of at least 5.

In various embodiments, the sample fluid is or is derived from a biological sample. Exemplary biological samples include any biological sample that contains phospholipids, such as biological fluids (e.g., whole blood samples, blood plasma samples, serum samples, etc.), biological tissues, biological matrices, cells (e.g., one or more types of cells), and cell culture supernatants, and foods that contain phospholipids (e.g., meats, whole grains, legumes, eggs, etc.), food extracts.

As indicated above, the methods of performing sample enrichment described herein include a step where a sample fluid that comprises at least one phospholipid and at least one target analyte is added to a sorbent (suitable sorbents are described in more detail below).

Such a process frequently referred to as a "loading" process, and commonly involves passing the sample fluid through a device that contains the sorbent (such devices are described in more detail below). During loading, the one or more target analytes, along with various non-target substances, including one or more phospholipids, are adsorbed onto the sorbent. Contact time and/or flow rate may be optimized for proper diffusion kinetics and binding of the one or more target analytes and the one or more phospholipids to the sorbent. If desired the sample fluid may be passed multiple times through the device.

In certain embodiments, for example, where the sorbent is not readily water-wettable, conditioning and equilibrating steps may optionally be performed prior to sample loading. For example, in an exemplary embodiment, the conditioning may be performed with methanol, ethanol, propanol, isopropyl alcohol, water and a mixture thereof, among other possibilities. For example, in an exemplary embodiment, the equilibrating solution may have an appropriate pH and solvent strength to provide equilibrated partitioning environments in the sorbent when the sample fluid is loaded. Exemplary equilibrating solution/solvent include, for example, water, an aqueous solution such as a buffer solution (e.g., a phosphate buffer solution), a water-miscible organic solvent solution and the like.

In certain embodiments, for example, where the sorbent is sufficiently water-wettable, conditioning and equilibrating may be omitted before sample loading.

In certain methods of performing sample enrichment described herein, including methods that employ a sorbent comprising a cation exchange component that comprises $H^+$ as a counter ion, prior to adding a washing solution that comprises a first organic solvent species, an aqueous solution comprising an acidic compound and a first salt species may be either (a) added to the sample fluid prior to adding the sample fluid to the sorbent or (b) added to the sorbent after loading the sorbent with the sample fluid.

In either of these intermediate steps, the acidic compound in the aqueous solution may be selected from a variety of acidic compounds, including one or more of the following: organic acids such as formic acid, acetic acid, propionic acid, butyric acid, oxalic acid, malonic acid, succinic acid and maleic acid, among others and including organic hydroxyacids such as glycolic acid, lactic acid, tartaric acid, malic acid, citric acid and gluconic acid, among others; and inorganic acids such as phosphoric acid, hydrochloric acid, or carbonic acid, among others.

The amount of acid in the aqueous solution may vary but is beneficially provided in an amount sufficient to provide the aqueous solution with a pH that is at least two pH units below a lowest $pK_a$ of the target analyte.

Salt species for using in conjunction with the present disclosure, including the first salt species in the aqueous solution, may be selected from a variety of salts, including salts that comprise (a) an anion selected from organic anions (those based on organic acids), such as formate, acetate, propionate, butyrate, oxalate, malonate, succinate, maleate, or glutarate, glycolate, lactate, malate, citrate, and gluconate, and other anionic species such as halides, nitrate, phosphate, sulfate, and sulfonates, among others and (b) a cation selected from ammonium cations, Group I metal cations, Group II metal cations, and cations based on amines (also referred to herein as an amine cation), such as methyl amine (methyl ammonium), methane diamine (methyl diammonium), ethyl amine (ethyl ammonium), ethyl diamine (ethyl diammonium), diethylamine (diethyl ammonium), diethanolamine (diethanol ammonium), tromethamine, choline, pyrrolidine (pyrrolidinium), piperazine (piperazinium), or pyridine (pyridinium), among others. In certain embodiments, the salt is ammonium formate.

The amount of salt in the aqueous solution may vary widely. In certain embodiments, the salt may be provided in an amount that produces an ionic strength ranging from 10-250 mM, where ionic strength is expressed by the equation, $$I = \frac{1}{2}\sum_i c_i z_i^2,$$

where $c_1$ is the molar concentration of any ion in solution, and $z_1$ is its valence. For salts consisting of an anion having a valence of 1 and a cation having a valence of 1, the ionic strength of the solution is equal to the molar concentration of the dissolved salt.

After either of these intermediate steps, the washing solution that comprises the first organic solvent species is contacted with the sorbent thereby desorbing at least a portion of the at least one phospholipid from the sorbent. In this way, non-target substances, including the one or more phospholipids are separated from the one or more target analytes, which are bound to the sorbent, thereby resulting in the elution of the non-target substances, while allowing the one or more target analytes to remain retained on the sorbent.

In certain other methods of performing sample enrichment described herein, including methods that employ a sorbent comprising a cation exchange component comprising a counter-ion that is not $H^+$ (e.g., counter-ion selected from a Group I metal cation, a Group II metal cation, an ammonium cation, and an amine cation), the washing solution that comprises the first organic solvent species may be contacted with the sorbent, without an intermediate step employing an aqueous solution comprising an acidic compound and a first salt species as described above. As above, the washing solution that comprises the first organic solvent species desorbs at least a portion of the at least one phospholipid from the sorbent, thereby separating non-target substances, including the one or more phospholipids, from the one or more target analytes, which are bound to the sorbent, resulting in the elution of the non-target substances, while allowing the one or more target analytes to remain retained on the sorbent.

A variety of organic solvent species may be used in the washing solutions of the present disclosure, including one or more of the following, among others: methanol, ethanol, 1-propanol, 2-propanol, acetonitrile, acetone, ethyl acetate, methyl ethyl ketone, and tetrahydrofuran. In certain beneficial embodiments, the organic solvent species is methanol.

After separating the washing solution from the sorbent, an elution solution that comprises (a) a basic compound or a salt species (also referred to herein as a second salt species in some embodiments), which may be the same as or different from the first salt species described above, and (b) an organic solvent species (also referred to herein as a second organic solvent species), which may be the same as or different from the first organic solvent species described above, is contacted with the sorbent, thereby desorbing at least a portion of the at least one target analyte from the sorbent and forming a solution of the target analyte in the elution solution.

The base in the elution solution may be selected from a variety of bases. The amount of base in the elution solution may vary but is beneficially provided in an amount sufficient to provide the elution solution with a pH that is at least two pH units above a highest $pK_a$ of the target analyte. Examples of bases may be selected from one or more of the following, among others: ammonium hydroxide ($NH_4OH$), alkali metal hydroxides (e.g., LiOH, NaOH, KOH, RbOH, etc.), alkaline earth metal hydroxides (e.g., $Mg(OH)_2$, $Ca(OH)_2$, $Sr(OH)_2$, etc.), organic bases (e.g., triethylamine), and combinations thereof. In certain beneficial embodiments, a volatile base such as ammonium hydroxide is particularly beneficial.

The second salt species in the elution solution may be selected from a variety of salts, including salts that comprise (a) an anion selected from organic anions (those based on organic acids), such as formate, acetate, propionate, butyrate, oxalate, malonate, succinate, maleate, or glutarate, glycolate, lactate, malate, citrate, and gluconate, among others and (b) a cation selected from ammonium cations, and cations based on amines, such as methyl amine (methyl ammonium), methane diamine (methyl diammonium), ethyl amine (ethyl ammonium), ethyl diamine (ethyl diammonium), diethylamine (diethyl ammonium), diethanolamine (diethanol ammonium), tromethamine, choline, pyrrolidine (pyrrolidinium), pyrrole (pyrrolium), piperazine (piperazinium), or pyridine (pyridinium), among others. In certain embodiments, the salt is ammonium formate. The amount of salt in the elution solution may vary but is beneficially provided in an amount sufficient to effectively elute the analyte.

A variety of second organic solvent species may be used in the elution solutions of the present disclosure, which solvent species may be same as or different from those of the washing solution (also referred to as the first organic solvent species) and include one or more of the following, among others: methanol, ethanol, 1-propanol, 2-propanol, acetonitrile, acetone, ethyl acetate, methyl ethyl ketone, and tetrahydrofuran. In certain beneficial embodiments, the organic solvent species is methanol.

In particular beneficial embodiments, the elution solution comprises 2-10 vol % concentrated $NH_4OH$ and 90-98 vol % methanol.

After being eluted from the sorbent, further processing of the one or more target analytes may include, for example, identifying, quantifying, or otherwise processing the one or more target analytes.

In various embodiments, methods described herein may further comprise analyzing samples using analytical instruments and/or techniques, for example, liquid chromatography (LC), including high performance liquid chromatography (HPLC) and ultra-high performance liquid chromatography (UHPLC), mass spectrometry (MS), including electrospray ionization mass spectrometry (ESI-MS), or a combination thereof. For instance, in some embodiments, the processed samples may be analyzed using liquid chromatography, such as HPLC or UHPLC, in combination with mass spectrometry, such as ESI-MS, examples of which include liquid chromatography-mass spectrometry (LC-MS) techniques and liquid chromatography-mass spectrometry/mass spectrometry (LC-MS/MS) techniques. In certain cases, analytical samples may be evaporated to dryness, and then reconstituted in another solution before being injected into a liquid chromatography system.

As noted above, sorbents for use in the present disclosure include sorbents having a hydrophobic component and a cation exchange component. In some embodiments, the sorbents comprise an organic polymer having a hydrophobic component and a cation exchange component. In certain embodiments, the cation-exchange component comprises $H^+$ as a counter-ion. In certain embodiments, the cation-exchange component comprises a counter-ion that is not E (e.g., a Group I metal cation, a Group II metal cation, an ammonium cation, an amine cation, etc.).

As used herein, "hydrophobic" means lacking an affinity for, repelling, or failing to adsorb or absorb water, whereas "hydrophilic" means having an affinity for, attracting, adsorbing or absorbing water, As used herein, "organic polymers" are organic molecules containing multiple copies (e.g., from 5 to 10 to 25 to 50 to 100 to 250 to 500 to 1000 or more copies) of one or more constitutional units, commonly referred to as organic monomers. As used herein, "organic monomers" may refer to free monomers and to those incorporated into polymers, with the distinction being clear from the context in which the term is used. As a specific example, the following monomer,

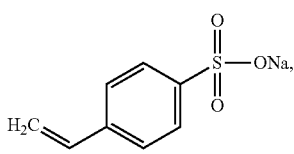

and the following incorporated monomer,

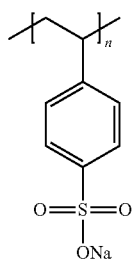

(where n is 1), may each be referred to herein as "a styrene sulfonate monomer." It is noted that incorporated monomers are named independently of the monomer that was polymerized to form the polymer. For instance, in the preceding example, the incorporated styrene sulfonate monomer may, in theory, be formed from a free styrene sulfonate monomer or from a styrene monomer that is first polymerized and later subjected to a sulfonation process. In either case, the incorporated organic monomer is referred to herein as a styrene sulfonate monomer.

Organic polymers may take on a number of configurations, which may be selected, for example, from linear, cyclic and branched configurations, among others. Branched configurations include star-shaped configurations (e.g., configurations in which three or more chains emanate from a single branch point), comb configurations (e.g., configurations having a polymer backbone and a plurality of side chains, also referred to as "graft" configurations), dendritic configurations (e.g., arborescent and hyperbranched polymers), networked (e.g., crosslinked) configurations and so forth.

As used herein, "organic homopolymers" are polymers that contain multiple copies of a single organic monomer. As used herein, "organic copolymers" are organic polymers that contain multiple copies of at least two dissimilar organic monomers, examples of which include random, statistical, gradient, periodic (e.g., alternating) and block copolymers.

In some embodiments, the organic polymer having a hydrophobic component and a cation exchange component, may be, for example, an organic copolymer comprising a hydrophobic organic monomer and an organic monomer having a cation-exchange group. In some embodiments, the organic copolymer comprising the hydrophobic organic monomer and the organic monomer having the cation-exchange group may further comprise a hydrophilic organic monomer, thereby improving the water wettability of the copolymer. Exemplary examples are described in U.S. Pat. Nos. 7,232,520 and 7,442,299.

In certain embodiments, the hydrophobic monomer may be selected from alkene monomers (e.g., butadiene), monomers having a straight chain C2-C18-alkyl group, monomers having a branched chain C3-C18-alkyl group, monomers having a C6-C18 monocyclic or multicyclic, saturated, unsaturated or aromatic carbocyclic group, e.g., a phenyl group, or a phenylene group. Specific examples of hydrophobic monomers include, for example, divinylbenzene, styrene, or ethylvinylbenzene.

In certain embodiments, the organic monomer having the cation-exchange group may be selected from organic monomers that comprise one or more sulfonate groups. In particular embodiments, the organic monomer having the cation-exchange group may be a divinylbenzene monomer that comprises one or more sulfonate groups. In certain embodiments, the cation-exchange group comprises $H^+$ as a counter-ion. In certain embodiments, the cation-exchange group comprises a counter-ion that is not $H^+$ (e.g., a Group I metal cation, a Group II metal cation, an ammonium cation, an amine cation, etc.).

In certain embodiments, the hydrophilic monomer may be selected from monomers having an amide group, monomers having an ester group, monomers having a carbonate group, monomers having a carbamate group, monomers having a urea group, monomers having a hydroxyl group, and monomers having a nitrogen-containing heterocyclic group, e.g., a saturated, unsaturated or aromatic heterocyclic group. Specific examples: include, for example, 2-vinylpyridine, 3-vinylpyridine, 4-vinylpyridine, vinylpyrrolidone, N-vinyl-piperidone, caprolactam, acrylates methyl acrylate, ethyl acrylate, etc.), alkyl methacrylates (e.g., methyl methacrylate, ethyl methacrylate, etc.), vinyl acetate, acrylamide, or methacrylamide.

Typically, the organic copolymer will comprise a multifunctional hydrophobic monomer such as divinylbenzene and/or a multifunctional hydrophilic monomer such as ethylene glycol dimethacrylate, methylene bisacrylamide or allyl methacrylate to provide crosslinks in the copolymer.

Instead of, or in addition to, sorbents that comprise an organic polymer having a hydrophobic component and a cation exchange component as described above, in some embodiments, a sorbent may be employed that is based on inorganic materials such as silica-based materials, alumina-based materials, titania-based materials, and zirconia-based materials. For example, such materials may be surface modified to include both a hydrophobic component (e.g., a C4 to C30 alkyl or aromatic component) and a cation exchange component (e.g., an alkylsulfonate, an aromatic sulfonate or an alkylphosphate).

Sorbents for use in the present disclosure may comprise sorbent particles, which may vary widely in size and may range, for example, from about 5 to about 100 μm in diameter, among other possible particle sizes. Sorbent particles for use in conjunction with the present disclosure may be porous or non-porous.

Devices in accordance with the present disclosure commonly include sorbents such as those described herein in a packed sorbent bed.

Devices in accordance with the present disclosure commonly include a housing having a chamber for accepting and holding sorbent. In various embodiments, the housing may be provided an inlet and an outlet.

The construction materials for the housing include inorganic materials, for instance, metals such as stainless steel and ceramics such as glass, as well as synthetic polymeric materials such as polyethylene, polypropylene, polyether ether ketone (PEEK), and polytetrafluoroethylene, among others.

In certain embodiments, the device may include one or more filters which act to hold the sorbent in a housing. Exemplary filters may be, for example, in a form of membrane, screen, frit or spherical porous filter.

In certain embodiments, a solution received in the housing may flow into the sorbent spontaneously, for example, capillary action. Alternatively, the flow may be generated through the sorbent by external forces, such as gravity or centrifugation, or by applying a vacuum to an outlet of the housing or positive pressure to an inlet of the housing.

Specific examples of housings for use in the present disclosure include, for example, a syringe, an injection cartridge, a column (e.g., a microbore column, capillary column or nanocolumn), a multi-well device such as a 4 to 8-well rack, a 4 to 8-well strip, a 48 to 96-well plate, a 96 to 384-well micro-elution plate, micro-elution tip devices, including a 4 to 8-tip micro-elution strip, a 96 to 384-micro-elution tip array, a single micro-elution pipet tip, a thin layer plate, a microtiter plate, a spin tube or a spin container.

Multi-well formats are commonly used with robotic fluid dispensing systems. Typical multi-well formats include 48-, 96-, and 384-well standard plate formats, although other formats are clearly possible.

Kits may also be provided which comprise a sorbent as described elsewhere herein and one or more of any of the following: (a) an aqueous solution that comprises an acidic compound and a first salt species as described elsewhere herein, (b) an organic solution comprising a first organic solvent species as described elsewhere herein, (c) an elution solution that comprises (i) a basic compound or a second salt species and (ii) a second organic solvent species as described elsewhere herein, (d) a collection plate or collection vial, (e) a cap mat, (f) calibration and reference standards, and (g) instructions for use. The sorb ent may be disposed in a housing, for example, in a column, a single-use cartridge, a multi-well strip, a multi-well plate, or other housing as described elsewhere herein.

Further aspects of the present disclosure are provided in the following enumerated paragraphs:

Aspect A1. A method of performing a sample enrichment procedure, the method comprising: (a) adding a sample fluid that comprises at least one phospholipid and at least one target analyte to a sorbent comprising an organic copolymer that comprises a hydrophobic organic monomer, a hydrophilic organic monomer and an organic monomer comprising a cation-exchange group thereby resulting in sorbent with adsorbed phospholipid and adsorbed target analyte; (b) adding an aqueous solution comprising an acidic compound and a first salt species (i) to the sample fluid prior to adding the sample fluid to the sorbent or (ii) to the sorbent after adding the sample fluid to the sorbent; (c) adding an organic solution comprising a first organic solvent species to the sorbent thereby desorbing at least a portion of the phospholipid from the sorbent; and (d) adding an elution solution that comprises (i) a basic compound or a second salt species, which may be the same as or different from the first salt species, and (ii) a second organic solvent species, which may be the same as or different from the first organic solvent species, to the sorbent, thereby desorbing at least a portion of the target analyte from the sorbent and forming a solution of the target analyte in the elution solution.

Aspect A2. The method of aspect A1, wherein the target analyte is a base with a $pK_a$ of at least 5.

Aspect A3. The method of any of aspects A1-A2, wherein the aqueous solution comprises the acidic compound in an amount sufficient to provide the aqueous solution with a pH that is at least two pH units below a lowest $pK_a$ of the target analyte.

Aspect A4. The method of any of aspects A1-A3, wherein the acidic compound is selected from an organic acid, phosphoric acid, hydrochloric acid, or carbonic acid.

Aspect A5. The method of any of aspects A1-A4, wherein the first salt species dissociates into an organic acid anion or an inorganic anion and a cation selected from a Group I metal cation, a Group II metal cation, an ammonium cation, and an amine cation.

Aspect A6. The method of aspect A5, wherein the organic acid anion is selected from formate, acetate, propionate, butyrate, oxalate, malonate, succinate, maleate, glutarate, glycolate, lactate, malate, citrate and gluconate.

Aspect A7. The method of any of aspects A1-A6, wherein the aqueous solution comprises the salt in an amount corresponding to an ionic strength ranging from 10-250 mM.

Aspect A8. The method of any of aspects A1-A7, wherein the first organic solvent species of the organic solution is selected from methanol, ethanol, 1-propanol, 2-propanol, acetonitrile, acetone, ethyl acetate, methyl ethyl ketone, tetrahydrofuran and blends thereof.

Aspect A9. The method of any of aspects A1-A8, wherein the first organic solvent species is methanol.

Aspect A10. The method of any of aspects A1-A9, wherein the second organic solvent species is selected from methanol, ethanol, 1-propanol, 2-propanol, acetonitrile, acetone, ethyl acetate, methyl ethyl ketone, tetrahydrofuran and blends thereof.

Aspect A11. The method of any of aspects A1-A10, wherein the second organic solvent species is methanol.

Aspect A12. The method of any of aspects A1-A11, wherein the elution solution comprises the basic compound in an amount sufficient to provide the elution solution with a pH that is at least two pH units above a highest $pK_a$ of the target analyte.

Aspect 13. The method of any of aspects A1-A12, wherein the basic compound of the elution solution is selected from ammonium hydroxide ($NH_4OH$), NaOH, KOH, triethylamine and combinations thereof.

Aspect A14. The method of any of aspects A1-A13, wherein the elution solution comprises 2-10 vol % concentrated $NH_4OH$ and 90-98 vol % methanol.

Aspect A15. The method of any of aspects A1-A11, wherein the elution solution comprises the second salt species in an amount sufficient to elute the analyte.

Aspect A16. The method of any of aspects A1-A11 and A15 wherein the second salt species dissociates into an organic acid anion and a cation selected from an ammonium cation and an amine cation.

Aspect A17. The method of any of aspects A1-A11 and A15-A16, wherein the organic acid anion is selected from formate, acetate, propionate, butyrate, oxalate, malonate, succinate, maleate, glutarate, glycolate, lactate, malate, citrate and gluconate.

Aspect A18. The method of any of aspects A15-A17, wherein the elution solution comprises the second salt species in an amount corresponding to an ionic strength ranging from 10-250 mM.

Aspect A19. The method of any of aspects A15-A18, wherein the elution solution comprises 50-250 mM ammonium formate in methanol.

Aspect A20. The method of any of aspects A1-A19, wherein the sample fluid comprises a biological sample selected from a whole blood sample, a plasma sample, a serum sample, a food sample, and a food extract sample.

Aspect A21. The method of any of aspects A1-A20, wherein the aqueous solution comprising the acidic compound and the first salt species is added to the sample fluid prior to adding the sample fluid to the sorbent.

Aspect A22. The method of any of aspects A1-A20, wherein the aqueous solution comprising the acidic compound and the first salt species is added to the sorbent after loading the sorbent with the sample fluid.

Aspect A23. The method of any of aspects A1-A22 wherein the hydrophilic organic monomer of the organic copolymer is selected from organic monomers comprising an amide group, organic monomers comprising an ester group, organic monomers comprising a carbonate group, organic monomers comprising a carbamate group, organic monomers comprising a urea group, organic monomers comprising a hydroxyl group, and organic monomers that comprise a nitrogen-containing heterocyclic group.

Aspect A24. The method of any of aspects A1-A23 wherein the hydrophobic organic monomer of the organic copolymer is selected from organic monomers comprising a straight chain C2-C18-alkyl group, organic monomers comprising a branched chain C3-C18-alkyl group, organic monomers comprising a C4-C18 monocyclic or multicyclic, saturated, unsaturated or aromatic carbocyclic group.

Aspect A25. The method of any of aspects A1-A24 wherein the organic monomer comprising a cation-exchange group comprises a cation-exchange group selected from a sulfonate group and a phosphate group.

Aspect A26. The method of any of aspects A1-A25 wherein the hydrophilic organic monomer is selected from N-vinyl pyrrolidone and N-vinyl caprolactam, wherein the hydrophobic organic monomer is divinylbenzene, and wherein the cation-exchange group is a sulfonate group.

Aspect B 1. A method of performing a sample enrichment procedure, the method comprising: (a) adding an aqueous solution comprising an acidic compound and a first salt species to a sample fluid that comprises at least one phospholipid and at least one target analyte, thereby forming a pretreated sample; (b) adding the pretreated sample to a sorbent, thereby resulting in sorbent with adsorbed phospholipid and adsorbed target analyte, wherein the sorbent comprises a hydrophobic component and a cation exchange component; (c) washing the sorbent in a single washing step wherein an organic solution comprising a first organic solvent species is added to the sorbent thereby desorbing at least a portion of the phospholipid from the sorbent; and (d) adding an elution solution that comprises (i) a basic compound or a second salt species, which may be the same as or different from the first salt species, and (ii) a second organic solvent species, which may be the same as or different from the first organic solvent species, to the sorbent, thereby desorbing at least a portion of the target analyte from the sorbent and forming a solution of the target analyte in the elution solution.

Aspect B2. The method of aspect B1, wherein the target analyte is a base with a $pK_a$ of at least 5.

Aspect B3. The method of any of aspects B1-B2, wherein the aqueous solution comprises the acidic compound in an amount sufficient to provide the aqueous solution with a pH that is at least two pH units below a lowest $pK_a$ of the target analyte.

Aspect B4. The method of any of aspects B1-B3, wherein the acidic compound is selected from an organic acid, phosphoric acid, hydrochloric acid, or carbonic acid.

Aspect B5. The method of any of aspects B1-B4, wherein the first salt species dissociates into an organic acid anion or an inorganic anion and a cation selected from a Group I metal cation, a Group II metal cation, an ammonium cation, and an amine cation.

Aspect B6. The method of aspect B5, wherein the organic acid anion is selected from formate, acetate, propionate, butyrate, oxalate, malonate, succinate, maleate, glutarate, glycolate, lactate, malate, citrate and gluconate.

Aspect B7. The method of any of aspects B1-B6, wherein the aqueous solution comprises the first salt species in an amount corresponding to an ionic strength ranging from 10-250 mM.

Aspect B8. The method of any of aspects B1-B7, wherein the first organic solvent species is selected from methanol, ethanol, 1-propanol, 2-propanol, acetonitrile, acetone, ethyl acetate, methyl ethyl ketone, tetrahydrofuran and blends thereof.

Aspect B9. The method of any of aspects B1-B8, wherein the first organic solvent species is methanol.

Aspect B10. The method of any of aspects B1-B9, wherein the second organic solvent species is selected from methanol, ethanol, 1-propanol, 2-propanol, acetonitrile, acetone, ethyl acetate, methyl ethyl ketone, tetrahydrofuran and blends thereof.

Aspect B11. The method of any of aspects B1-B10, wherein the second organic solvent species is methanol.

Aspect B12. The method of any of aspects B1-B11, wherein the elution solution comprises the basic compound in an amount sufficient to provide the elution solution with a pH that is at least two pH units above a highest $pK_a$ of the target analyte.

Aspect B13. The method of any of aspects B1-B12, wherein the basic compound of the elution solution is selected from ammonium hydroxide ($NH_4OH$), NaOH, KOH, triethylamine and combinations thereof.

Aspect B14. The method of any of aspects B1-B13, wherein the elution solution comprises 2-10 vol % concentrated $NH_4OH$ and 90-98 vol % methanol.

Aspect B15. The method of any of aspects B1-B11, wherein the elution solution comprises the second salt species in an amount sufficient to elute the analyte.

Aspect B16. The method of any of aspects B1-B11 and B15 wherein the second salt species dissociates into an organic acid anion and a cation selected from an ammonium cation and an amine cation.

Aspect B17. The method of any of aspects B1-B11 and B15-B16, wherein the organic acid anion is selected from formate, acetate, propionate, butyrate, oxalate, malonate, succinate, maleate, glutarate, glycolate, lactate, malate, citrate and gluconate.

Aspect B18. The method of any of aspects B15-B17, wherein the elution solution comprises the second salt species in an amount corresponding to an ionic strength ranging from 10-250 mM.

Aspect B19. The method of any of aspects B15-B18, wherein the elution solution comprises 50-250 mM ammonium formate in methanol.

Aspect B20. The method of any of aspects B1-B19, wherein the sample fluid comprises a biological sample selected from a whole blood sample, a plasma sample, a serum sample, a food sample, and a food extract sample.

Aspect B21. The method of any of aspects B1-B20, wherein the aqueous solution comprising the acidic compound and the first salt species is added to the sample fluid prior to adding the sample fluid to the sorbent.

Aspect B22. The method of any of aspects B1-B20, wherein the aqueous solution comprising the acidic compound and the first salt species is added to the sorbent after loading the sorbent with the sample fluid.

Aspect B23. The method of any of aspects B1-B22, wherein the sorbent comprises an organic copolymer comprising a hydrophobic organic monomer and an organic monomer comprising a cation-exchange group.

Aspect B24. The method of aspect B23 wherein the hydrophobic organic monomer is selected from organic monomers comprising a straight chain C2-C18-alkyl group, organic monomers comprising a branched chain C3-C18-alkyl group, organic monomers comprising a C4-C18 monocyclic or multicyclic, saturated, unsaturated or aromatic carbocyclic group.

Aspect B25. The method of any of aspects B23-B24, wherein the organic monomer comprising a cation-exchange group comprises a cation-exchange group selected from a sulfonate group and a phosphate group.

Aspect B26. The method of any of aspects B23-B25, wherein the organic copolymer comprises a hydrophilic organic monomer.

Aspect B27. The method of aspect B26, wherein the hydrophilic organic monomer is selected from organic monomers comprising an amide group, organic monomers comprising an ester group, organic monomers comprising a carbonate group, organic monomers comprising a carbamate group, organic monomers comprising a urea group, organic monomers comprising a hydroxyl group, and organic monomers that comprise a nitrogen-containing heterocyclic group.

Aspect B28. The method of aspect B26, wherein the hydrophilic organic monomer is selected from N-vinyl pyrrolidone and N-vinyl caprolactam, wherein the hydrophobic organic monomer is divinylbenzene, and wherein the cation-exchange group is a sulfonate group.

Aspect C1. A kit comprising (a) a sorbent comprising a hydrophobic moiety and a cation exchange moiety and (b) an aqueous solution comprising an acidic compound and a first salt species.

Aspect C2. The kit of aspect C1, further comprising one or more additional components selected from any of the following: (a) a first organic solution comprising a first organic solvent species, (b) a second organic solution that comprises (i) a second organic solvent species, which may be the same as or different from the first organic solvent species, and (ii) a basic compound or a second salt species, which may be the same as or different from the first salt species, (c) a collection plate or collection vials, (d) a cap mat, (e) calibration and reference standards, (e) identification tagging for each component, and (f) instructions for use.

Aspect C3. The kit of any of aspects C1-C2, wherein the sorbent is provided in a multi-well strip, a multi-well plate, a column, or a cartridge.

Aspect C4. The kit of any of aspects C1-C3, wherein the acidic compound is selected from an organic acid, phosphoric acid, hydrochloric acid, or carbonic acid.

Aspect C5. The kit of any of aspects C1-C4, wherein the first salt species dissociates into an organic acid anion or an inorganic anion and a cation selected from a Group I metal cation, a Group II metal cation, an ammonium cation, and an amine cation.

Aspect C6. The kit of aspect C5, wherein the organic acid anion is selected from formate, acetate, propionate, butyrate, oxalate, malonate, succinate, maleate, glutarate, glycolate, lactate, malate, citrate and gluconate.

Aspect C7. The kit of any of aspects C1-C6, wherein the aqueous solution comprises the salt in an amount corresponding to an ionic strength ranging from 10-250 mM.

Aspect C8. The kit of any of aspects C2-C7, wherein the first organic solvent species of the first organic solution is selected from methanol, ethanol, 1-propanol, 2-propanol, acetonitrile, acetone, ethyl acetate, methyl ethyl ketone, tetrahydrofuran and blends thereof.

Aspect C9. The kit of any of aspects C2-C8, wherein the first organic solvent species is methanol.

Aspect C10. The kit of any of aspects C2-C9, wherein the second organic solvent species of the second organic solution is selected from methanol, ethanol, 1-propanol, 2-propanol, acetonitrile, acetone, ethyl acetate, methyl ethyl ketone, tetrahydrofuran and blends thereof.

Aspect C11. The kit of any of aspects C2-C10, wherein the second organic solvent species is methanol.

Aspect C12. The kit of any of aspects C2-C11, wherein the basic compound is in an amount sufficient to provide the second organic solution with a pH that is at least two pH units above a highest $pK_a$ of the target analyte.

Aspect C13. The kit of any of aspects C2-C12, wherein the basic compound of the second organic solution is selected from ammonium hydroxide ($NH_4HO$), NaOH, KOH, triethylamine and combinations thereof.

Aspect C14. The kit of any of aspects C2-C13, wherein the second organic solution comprises 2-10 vol % concentrated $NH_4OH$ and 90-98 vol % methanol.

Aspect C15. The method of any of aspects C1-C11, wherein the elution solution comprises the second salt species in an amount sufficient to elute the analyte.

Aspect C16. The method of any of aspects C1-C11 and C15 wherein the second salt species dissociates into an organic acid anion and a cation selected from an ammonium cation and an amine cation.

Aspect C17. The method of any of aspects C1-C11 and C15-C16, wherein the organic acid anion is selected from formate, acetate, propionate, butyrate, oxalate, malonate, succinate, maleate, glutarate, glycolate, lactate, malate, citrate and gluconate.

Aspect C18. The method of any of aspects C15-C17, wherein the elution solution comprises the second salt species in an amount corresponding to an ionic strength ranging from 10-250 mM.

Aspect C19. The method of any of aspects C15-C18, wherein the elution solution comprises 50-250 mM ammonium formate in methanol.

Aspect C20. The kit of any of aspects C1-C19, wherein the sorbent comprises an organic copolymer that comprises a hydrophobic organic monomer and an organic monomer comprising a cation-exchange group.

Aspect C21. The kit of aspect C20, wherein the hydrophobic organic monomer is selected from organic monomers comprising a straight chain C2-C18-alkyl group, organic monomers comprising a branched chain C3-C18-alkyl group, organic monomers comprising a C4-C18 monocyclic or multicyclic, saturated, unsaturated or aromatic carbocyclic group.

Aspect C22. The kit of any of aspects C20-C21, wherein the organic monomer comprising a cation-exchange group comprises a cation-exchange group selected from a sulfonate group and a phosphate group.

Aspect C23. The kit of any of aspects C20-C22, wherein the organic copolymer further comprises a hydrophilic organic monomer.

Aspect C24. The kit of aspect C23 wherein the hydrophilic organic monomer is selected from organic monomers comprising an amide group, organic monomers comprising an ester group, organic monomers comprising a carbonate group, organic monomers comprising a carbamate group, organic monomers comprising a urea group, organic monomers comprising a hydroxyl group, and organic monomers that comprise a nitrogen-containing heterocyclic group.

Aspect C25. The kit of aspect C23, wherein the hydrophilic organic monomer is selected from N-vinyl pyrrolidone and N-vinyl caprolactam, wherein the hydrophobic organic monomer is divinylbenzene, and wherein the cation-exchange group is a sulfonate group.

Aspect D1. A method of performing a sample enrichment procedure, the method comprising: adding a sample fluid that comprises at least one phospholipid and at least one target analyte to a sorbent comprising a hydrophobic moiety and a cation exchange moiety comprising a counter-ion that is not H⁻ (e.g., a sorbent comprising an organic copolymer that comprises a hydrophobic organic monomer, a hydrophilic organic monomer and an organic monomer comprising a cation-exchange group, the cation-exchange group comprising a counter-ion that is not $H^+$), thereby resulting in sorbent with adsorbed phospholipid and adsorbed target analyte; adding a first organic solution comprising a first organic solvent to remove adsorbed phospholipid; and adding an elution solution that comprises (a) a basic compound or a first salt species and (b) a second organic solvent species to the sorbent, wherein the second organic solvent species may be the same as or different from the first organic solvent species, thereby desorbing at least a portion of the target analyte from the sorbent and forming a solution of the target analyte in the elution solution.

Aspect D2. The method of aspect D1, wherein the cation that is not $H^+$ is selected from a Group I metal cation, a Group II metal cation, an ammonium cation, and an amine cation.

Aspect D3. The method of any of aspects D1-D, wherein the cation exchange group comprises a sulfonate moiety.

Aspect D4. The method of any of aspects D1-D3, wherein the first and second organic solvent species are selected from methanol, ethanol, 1-propanol, 2-propanol, acetonitrile, acetone, ethyl acetate, methyl ethyl ketone, tetrahydrofuran and blends thereof.

Aspect D5. The method of any of aspects D1-D4, wherein the elution solution comprises the basic compound in an amount sufficient to provide the elution solution with a pH that is at least two pH units above a highest $pK_a$ of the target analyte.

Aspect D6. The method of any of aspects D1-D4, wherein the elution solution comprises the first salt species.

Aspect D7. The method of aspect D6, wherein the first salt species dissociates into (a) an organic acid anion or an inorganic anion and (b) a cation selected from a Group I metal cation, a Group II metal cation, an ammonium cation, and an amine cation.

Aspect D8. The method of aspect D7, wherein the organic acid anion is selected from formate, acetate, propionate, butyrate, oxalate, malonate, succinate, maleate, glutarate, glycolate, lactate, malate, citrate and gluconate or wherein the inorganic anion is selected from chloride, fluoride, bromide, hydroxide, nitrate, nitrite, sulfate and phosphate.

Aspect D9. The method of any of aspects D1-D4 and D6-D8, wherein the elution solution that comprises the first salt species comprises the first salt species in an amount corresponding to an ionic strength ranging from 10-250 mM.

Aspect D10. The method of any of aspects D1-D9, further comprising, after adding the sample fluid and before adding the first organic solution, adding an aqueous solution to the sorbent.

Aspect D11. The method of aspect D10, wherein the aqueous solution comprises an organic acid.

Aspect D12. The method of aspect D10, wherein the aqueous solution comprises one or more acids selected from the following: formic acid, acetic acid, propionic acid, butyric acid, oxalic acid, malonic acid, succinic acid maleic acid, glycolic acid, lactic acid, tartaric acid, malic acid, citric acid and gluconic acid, phosphoric acid, hydrochloric acid and carbonic acid.

Aspect D13. The method of any of aspects D1-D12, wherein the target analyte is a base with a $pK_a$ of at least 5.

Aspect D14. The method of any of aspects D1-D13, wherein the sample fluid comprises a biological sample selected from a whole blood sample, a plasma sample, a serum sample, a food sample, and a food extract sample.

Aspect E1. A kit comprising (a) a sorbent comprising a hydrophobic moiety and a cation exchange moiety comprising a counter-ion that is not $H^+$ and (b) one or more of the following (i) a first organic solution comprising a first organic solvent species, (ii) a second organic solution that comprises (iia) a second organic solvent species, which may be the same as or different from the first organic solvent species, and (iib) a basic compound or a salt species, (ii) a collection plate or collection vials, (iv) a cap mat, (v) calibration and reference standards, (vi) identification tagging for each component, and (vii) instructions for use.

Aspect E2. The kit of aspect E1, wherein the sorbent comprises an organic copolymer that comprises a hydrophobic organic monomer, a hydrophilic organic monomer and an organic monomer comprising the cation-exchange moiety.

Aspect E3. The kit of any one of aspects E1-E2, wherein the cation that is not is selected from a Group I metal cation, a Group II metal cation, an ammonium cation, and an amine cation.

Aspect E4. The kit of any of aspects E1-E3, wherein the sorbent is provided in a multi-well strip, a multi-well plate, a column, or a cartridge.

Example 1

A comparison of an existing Oasis MCX SPE protocol (Oasis Cartridge and 96-Well Plate Care and Use Manual, #716001391EN, section VII, Waters Corp., USA) and a protocol in accordance with the present disclosure (New Protocol 1) was carried out using 1 cc cartridges containing 30 mg of a 30 μm mixed mode reversed phase/strong cation exchange copolymer sorbent. The sorbent was prepared as described in U.S. Pat. Nos. 7,232,520 and 7,442,299. The sample was a solution of a phospholipid standard (L-α-phosphatidylcholine from egg yolk, Sigma catalog number P3556) dissolved in acetonitrile/methanol/water (80/1/19 v/v/v). The two protocols are shown in Table 1.

TABLE 1

| Step | New Protocol 1 | Oasis MCX Existing Protocol |
|---|---|---|
| Load | 1 mL of 1 mg/mL L-α-phosphatidylcholine in acetonitrile/methanol/water 80/1/19 v/v/v | 1 mL of 1 mg/mL L-α-phosphatidylcholine in acetonitrile/methanol/water 80/1/19 v/v/v |
| Wash 1 | 1 mL of 100 mM Ammonium Formate in 2% Formic Acid (aq) | 1 mL of 2% Formic Acid (aq) |
| Wash 2 | 1 mL of methanol | 1 mL of methanol |
| Elute | 1 mL of methanol + 5% NH$_4$OH | 1 mL of methanol + 5% NH$_4$OH |

100 mM ammonium formate in 2% aqueous formic acid is a solution prepared from ammonium formate and 98/2 v/v water/formic acid. 2% formic acid is a solution prepare by 98/2 v/v water/formic acid. 5% ammonium hydroxide in methanol is a solution containing 95/5 (v/v) methanol/concentrated NH$_4$OH. The solutions from each stage of the SPE protocol were analyzed using UPLC with UV detection, employing the conditions given in Table 2, which shows chromatographic conditions for phosphatidylcholine quantification and Table 3, which shows gradient conditions for phosphatidylcholine quantification.

The eluted solutions were neutralized by adding 35 µL of 98% formic acid (aq) before analyzing them, to avoid hydrolysis of the phosphatidylcholine catalyzed by the presence of ammonium hydroxide (NH$_4$OH). The relative concentrations of phosphatidylcholine in each fraction were determined by comparing the integrated peak areas to the sum of the areas for all four fractions. Eight replicates were carried out, and the average results were calculated.

TABLE 2

| | |
|---|---|
| Instrument | ACQUITY UPLC System/ACQUITY I-Class System Waters Corporation, Milford MA, USA |
| Column | ACQUITY UPLC BEH C$_8$ 1.7 µm 2.1 × 50 mm Waters Corporation, Milford MA, USA |
| Column Temperature | 60° C. |
| TUV | 200 nm (L-α-phosphatidylcholine Removal) 214 nm (Analyte Recovery) |
| Loop Size | 2 µL |
| Injection Type | Partial loop with needle overfill |
| Injection Volume | 1.4 µL |
| Strong Wash Solvent Volume | 150 µL |
| Weak Wash Solvent Volume | 500 µL |
| Sample Temperature | 22° C. |
| Sampling Rate | 40 (pts/sec) |
| Mobile Phase A1 (L-α-phosphatidylcholine Removal) | 100% water |
| Mobile Phase B1 (L-α-phosphatidylcholine Removal) | 100% acetonitrile |
| Mobile Phase A2 (Analyte Recovery) | 0.1% Trifluoroacetic acid in 100% water |
| Mobile Phase B2 (Analyte Recovery) | 0.075% Trifluoroacetic acid in 100% acetonitrile |
| Strong Needle Wash | 0.075% Trifluoroacetic acid in 100% acetonitrile |
| Weak Needle Wash | 10% acetonitrile/90% water v/v |
| Seal wash | 10% acetonitrile/90% water v/v |

TABLE 3

| Time (min) | Flow (mL/min) | % A1/% A2 | % B1/% B2 | Curve |
|---|---|---|---|---|
| Initial | 0.5 | 99.9 | 0.1 | Initial |
| 0.5 | 0.5 | 99.9 | 0.1 | 6 |
| 7.0 | 0.5 | 40 | 60 | 6 |
| 8.0 | 0.5 | 5 | 95 | 6 |
| 9.5 | 0.5 | 5 | 95 | 6 |
| 9.8 | 0.5 | 99.9 | 0.1 | 6 |
| 10.5 | 0.5 | 99.9 | 0.1 | 6 |

Table 4 shows the results of the phosphatidylcholine removal test (% of total phosphatidylcholine found in each fraction) using the two SPE protocols. The results show that with the existing Oasis MCX protocol, most of the phosphatidylcholine (84.5%) was found in the elute fraction. Most of the remainder (11.9%) was found in the load fraction, with very little found in the wash fractions. In contrast, with the New Protocol 1, most of the phosphatidylcholine (88.7%) was found in the wash 2 fraction. The load fraction contained 10.3% and the elute fraction only contained 0.8%. This demonstrates that the new protocol results in a 105-fold reduction in the phosphatidylcholine content of the elute fraction. This is the fraction that is typically analyzed using LC/MS/MS, where phosphatidylcholine may result in signal suppression or enhancement as well as column and instrument fouling.

TABLE 4

| Fraction | New Protocol 1 | Existing Oasis MCX Protocol |
|---|---|---|
| Load | 10.3% | 11.9% |
| Wash 1 | 0.2% | 0.3% |
| Wash 2 | 88.7% | 3.3% |
| Elute | 0.8% | 84.5% |

Example 2

A comparison of the existing Oasis MCX SPE protocol and New Protocol 1 was carried out where the sample was rat plasma (from Bioreclamation IVT, Westbury, N.Y., USA catalog number RATPLEDTA2) containing endogenous phospholipids and spiked with basic analytes (approximately 30 ng/well of each analyte). The SPE device was a 96-well SPE plate containing 10 mg per well of a 30 µm mixed mode reversed phase/strong cation exchange copolymer sorbent. The sorbent was prepared as described in U.S. Pat. Nos. 7,232,520 and 7,442,299. The protocols are shown in Table 5. 4% aq H$_3$PO$_4$ is a solution of 96/4 (v/v) water/concentrated H$_3$PO$_4$.

TABLE 5

| Step | New Protocol 1 | Existing Oasis MCX Protocol |
|---|---|---|
| Load | 100 µL of rat plasma plus 100 µL of 4% aq H$_3$PO$_4$ | 100 µL of rat plasma plus 100 µL of 4% aq H$_3$PO$_4$ |
| Wash 1 | 500 µL of 100 mM ammonium formate in 2% aq. formic acid | 500 µL of 2% aq. formic acid |
| Wash 2 | 500 µL methanol | 500 µL methanol |
| Elute | 2 × 150 µL 5% ammonium hydroxide in methanol | 2 × 150 µL 5% ammonium hydroxide in methanol |

The elute fractions were diluted 1:1 (v/v) with 50:50 methanol/water and analyzed using UPLC with MS/MS detection, employing the conditions given in Table 6, which shows system and method conditions for LC-MS/MS analyses, Table 7, which shows MRM conditions and transitions for basic analytes, and Table 8, which shows MRM conditions and transitions for the phosphatidylcholine class phospholipids (note: phosphatidylcholine quantitation used the TIC generated from all MRM transitions).

TABLE 6

| | |
|---|---|
| LC-MS/MS System: | ACQUITY I-Class UPLC with Xevo TQ-S Mass Spectrometer (MS/MS) Waters Corporation, Milford MA, USA |
| Column: | ACQUITY UPLC BEH $C_{18}$, 1.7 µm, 2.1 × 100 mm Waters Corporation, Milford MA, USA |
| Column Temperature: | 40° C. |
| Injection Volume: | 2.0 µL |
| Mobile Phases: | A1: 0.1% Formic Acid in Water B1: 0.1% Formic Acid in Acetonitrile |
| Needle Wash: | Strong- 2% Formic Acid in 1:1:1:1 Acetonitrile:Methanol:Isopropanol:Water (v/v) Weak- 90:10 Water:Acetonitrile (v/v) |
| Flow Rate: | 0.6 mL/min |
| Gradient: | Initial conditions: 2% B1. Hold for 1 min at 2% B1, linear ramp to 70% B1 over 3 minutes, linear ramp to 95% B1 over 0.1 min. Hold at 95% B1 for 2.9 min, return to initial conditions in 0.5 min, hold at 2% B1 for 0.5 min. |
| Run Time: | 8.0 minutes |
| Mass Spectrometer: | Xevo TQ-S |
| Capillary Voltage: | 1.0 kV |
| Cone Voltage: | See Table 7 and 8 |
| Desolvation Temperature: | 500° C. |
| Desolvation Gas Flow: | 1000 L/hr |
| Cone Gas Flow: | 150 L/hr |

TABLE 7

| Analyte | Cone Voltage (V) | Precursor Ion (m/z) | Product Ions (m/z) | Collision Energy (V) |
|---|---|---|---|---|
| Caffeine | 20 | 195.16 | 106.04 | 30 |
| Oxymorphone | 20 | 302.17 | 198.24 | 44 |
| Procainamide | 20 | 236.10 | 120.25 | 30 |
| Methamphetamine | 20 | 150.24 | 91.04 | 15 |
| Oxycodone | 20 | 316.10 | 241.08 | 30 |
| Codeine | 20 | 300.20 | 165.10 | 30 |
| 3,4-Methylenedioxy-methamphetamine (MDMA) | 20 | 194.21 | 105.18 | 22 |
| Clonidine | 20 | 230.09 | 159.94 | 30 |
| Risperidone | 20 | 411.32 | 110.17 | 50 |
| Propranolol | 20 | 260.26 | 116.23 | 18 |
| Amitriptyline | 20 | 278.23 | 91.19 | 24 |
| Verapamil | 20 | 455.44 | 150.17 | 44 |
| Phencyclidine (PCP) | 20 | 244.17 | 86.02 | 10 |

TABLE 8

| Precursor Ion (m/z) | Product Ion (m/z) | Cone Voltage (V) | Collision Energy (V) |
|---|---|---|---|
| 496.40 | 184.10 | 35 | 30 |
| 520.40 | 184.10 | 35 | 30 |
| 522.40 | 184.10 | 35 | 30 |
| 524.40 | 184.10 | 35 | 30 |
| 704.40 | 184.10 | 35 | 30 |
| 758.40 | 184.10 | 35 | 30 |
| 760.40 | 184.10 | 35 | 30 |
| 784.40 | 184.10 | 35 | 30 |
| 786.40 | 184.10 | 35 | 30 |
| 806.40 | 184.10 | 35 | 30 |
| 808.40 | 184.10 | 35 | 30 |

Recoveries were calculated from the ratio of pre-spiked to post-spiked peak areas. For each protocol, replicates were run (n=4 for analytes, n=8 for phosphatidylcholine). The average analyte recoveries and phosphatidylcholine amounts by peak area in the Elute fraction are reported here.

Figure 2:
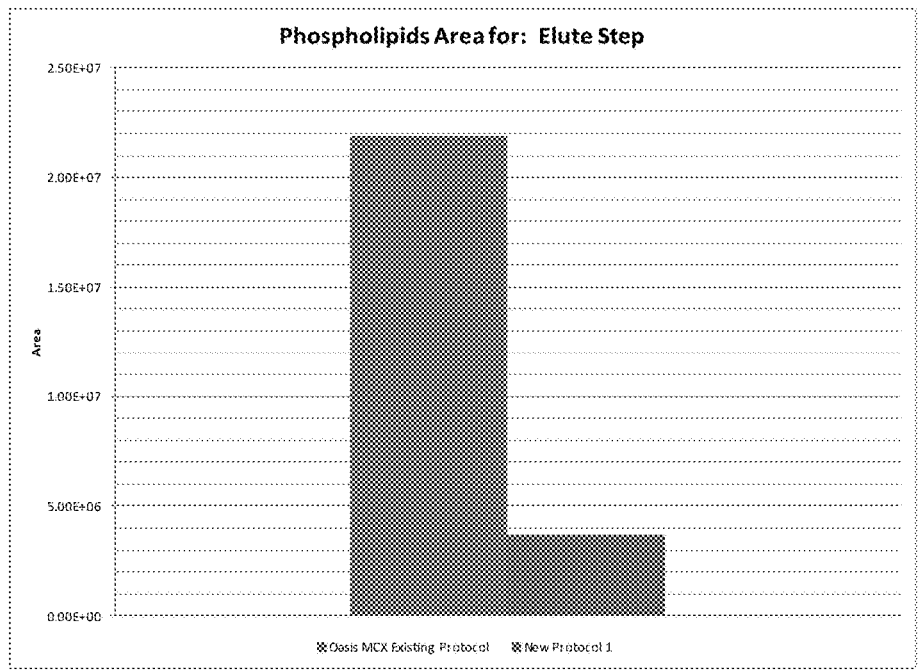
FIG. 2 shows a comparison of the elute fraction phosphatidylcholine peak areas for the Existing Oasis MCX Protocol and the New Protocol 1.

The results are summarized in FIG. 1, which is a comparison of the elute fraction analyte % recoveries for the Existing Oasis MCX Protocol and the New Protocol 1, and FIG. 2, which is a comparison of the elute fraction phosphatidylcholine peak areas for the Existing Oasis MCX Protocol and the New Protocol 1. As seen in these figures, New Protocol 1 gives over a 5-fold decrease in the amount of phosphatidylcholine present in the Elute fraction relative to the Existing Oasis MCX Protocol, while providing equivalent analyte recoveries, compared to the existing protocol.

Example 3

A comparison of the New Protocol 1, New Protocol 2a and New Protocol 2b was carried out where the sample was rat plasma (from Bioreclamation IVT, catalog number RATPLEDTA2) containing endogenous phospholipids and spiked with basic analytes (approximately 30 ng/well of each analyte). The SPE device was a 96-well SPE plate containing 10 mg per well of a 30 µm mixed mode reversed phase/strong cation exchange copolymer sorbent. The sorbent was prepared as described in U.S. Pat. Nos. 7,232,520 and 7,442,299. The protocols are shown in Table 9.

TABLE 9

| Step | New Protocol 1 | New Protocol 2a | New Protocol 2b |
|---|---|---|---|
| Load | 100 µL of rat plasma plus 100 µL of 4% aq $H_3PO_4$ | 100 µL of rat plasma plus 100 µL of 200 mM ammonium formate in 4% aq $H_3PO_4$ | 100 µL of rat plasma plus 100 µL of 200 mM ammonium formate in 4% Formic Acid |
| Wash 1 | 500 µL of 100 mM ammonium formate in 2% aq. formic acid | (not applicable) | (not applicable) |
| Wash 2 | 500 µL methanol | 500 µL methanol | 500 µL methanol |
| Elute | 2 × 150 µL 5% ammonium hydroxide in methanol | 2 × 150 µL 5% ammonium hydroxide in methanol | 2 × 150 µL 5% ammonium hydroxide in methanol |

The elute fractions were diluted 1:1 (v/v) with 50:50 methanol/water and analyzed by UPLC with MS/MS detection, using the conditions given in Tables 6, 7 and 8 (above). Recoveries were calculated from the ratio of pre-spiked to post-spiked peak areas. For each protocol, replicates were run (n=4 for analytes, n=8 for phosphatidylcholine). The average analyte recoveries and phosphatidylcholine amounts by peak area in the elute fraction are reported here.

Figure 3:
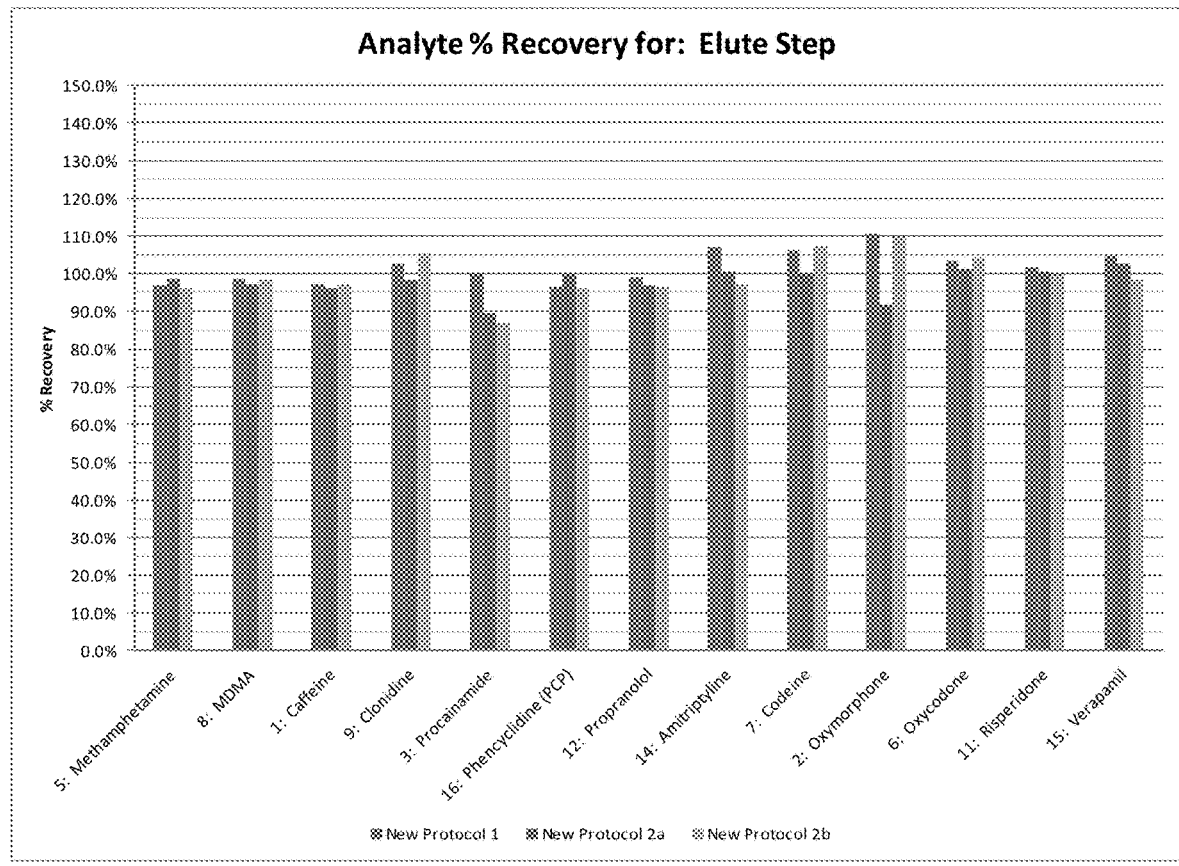
FIG. 3 shows a comparison of the elute step analyte % recoveries for the New Protocol 1, New Protocol 2a and New Protocol 2b.
Figure 4:
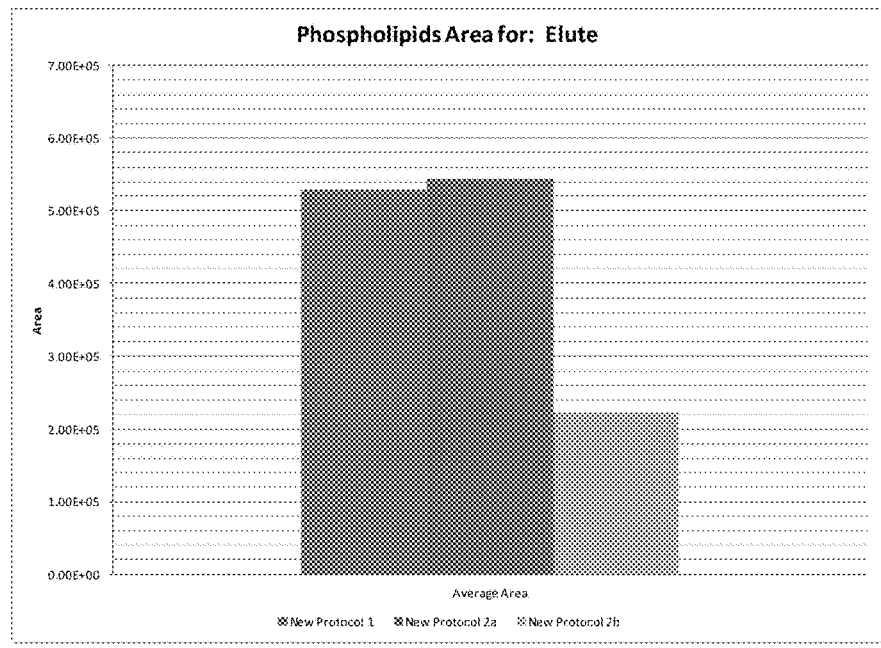
FIG. 4 shows a comparison of the elute fraction phosphatidylcholine peak areas for the New Protocol 1, New Protocol 2a and New Protocol 2b.

The results are summarized in FIG. 3, which shows a comparison of the elute step analyte % recoveries for the New Protocol 1, New Protocol 2a and New Protocol 2b, and FIG. 4, which shows a comparison of the elute fraction phosphatidylcholine peak areas for the New Protocol 1, New Protocol 2a and New Protocol 2b.

Regarding the phosphatidylcholine levels, New Protocol 2a gave results similar to New Protocol 1 while New Protocol 2b gave a level that was lower by a factor of approximately two. For the analyte recoveries, New Protocol 2a and 2b gave equivalent results to New Protocol 1.

Example 4

In New Protocol 3, a salt is added to the methanol wash solution. A series of experiments were carried out to determine the ammonium formate concentrations that are best for removing phosphatidylcholine while retaining the analytes. The protocols are described in Table 10.

TABLE 10

| Step | Oasis MCX Existing Protocol | New Protocol 3 |
|---|---|---|
| Load | 1 mL of sample | 1 mL of sample |
| Wash 1 | 1 mL of 2% Formic Acid (aq) | 1 mL of 2% Formic Acid (aq) |
| Wash 2 | 1 mL of methanol | 1 mL of methanol + Ammonium Formate (10 to 100 mM) |
| Elute | 1 mL of methanol + 5% NH$_4$OH | 1 mL of methanol + 5% NH$_4$OH |

For the phosphatidylcholine level tests, the sample was a solution of L-α-phosphatidylcholine from egg yolk (Sigma catalog number P3556) dissolved in acetonitrile/methanol/water (80/1/19 v/v/v). The elute solutions were neutralized by adding 35 μL of 98% formic acid (aq) before analyzing them, to avoid hydrolysis of the phosphatidylcholine catalyzed by the presence of ammonium hydroxide (NH$_4$OH). The concentrations of phosphatidylcholine in each fraction were determined by comparing the integrated peak areas to those of 1 mg/mL L-α-phosphatidylcholine in acetonitrile/methanol/water 80/1/19 v/v/v. For the analyte recovery tests, the sample was isotonic saline diluted 1:1 v/v with 4% H$_3$PO$_4$ (aq) spiked with 5.5 μg/mL amphetamine, 5.9 μg/mL metoprolol and 3.3 μg/mL amitriptyline. Recoveries were calculated from the ratio of pre-spiked to post-spiked peak areas. For each protocol, 4 replicates were run. The elute fractions were analyzed using UPLC with UV detection, with the separation conditions described in Tables 2 and 3 (see above).

Figure 5:
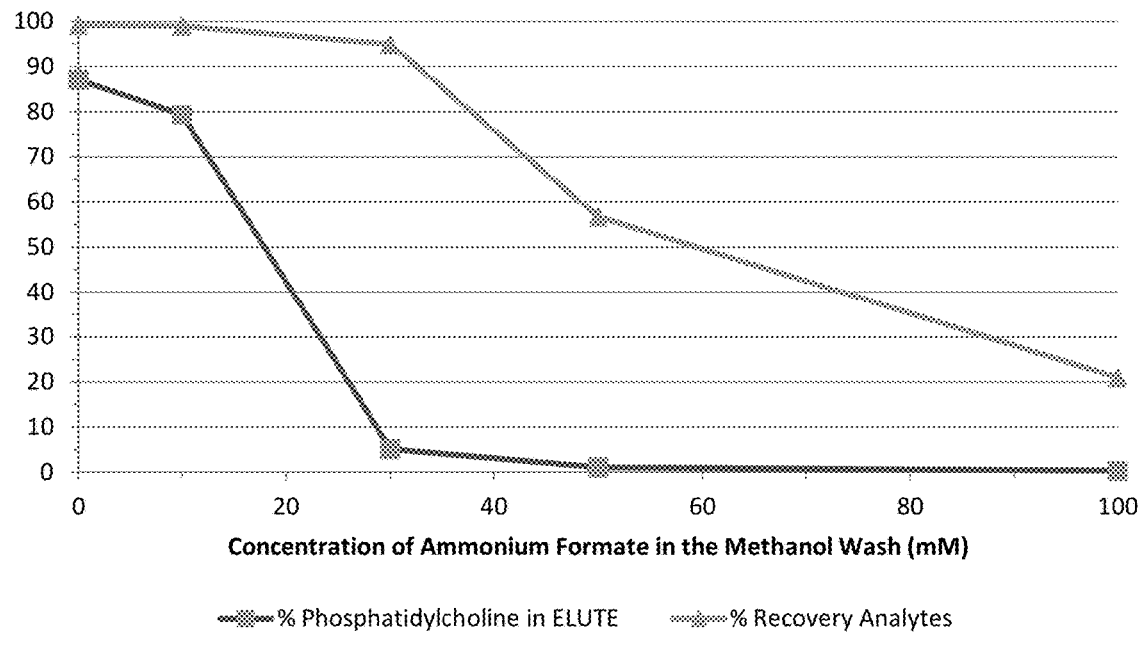
FIG. 5 shows a comparison of phosphatidylcholine level and analyte recovery using varying amounts of ammonium formate in the methanol wash step for new protocol 3.

FIG. 5 shows a comparison of phosphatidylcholine level and analyte recovery using varying amounts of ammonium formate in the methanol wash step for New Protocol 3. As seen from this figure, the results reveal that 30 mM is a pivotal concentration for both phosphatidylcholine removal and analyte recovery. An ammonium formate concentration of 30 mM was found to achieve a low level of phosphatidylcholine in the elute fraction. However, analyte recovery decreases as the ammonium formate concentration is increased beyond this level.

Example 5

A 2 gram batch of modified Oasis MCX (Oasis MCX-NH$_4^+$) sorbent was prepared as follows. Oasis MCX 30 μm (Waters Corporation) was suspended in 200 mL of 1 molar ammonium formate, pH 3 for 1.5 to 2 hours, then filtered through a 10 μm filter and washed 2× using 250 mL of DI water. The material was allowed to air dry for 72 hours in a hood.

An initial experiment was carried out using the 30 μm Oasis MCX-NH$_4^+$ sorbent in 1 cc/30 mg cartridge format. The sample was a solution of a phospholipid standard (L-α-phosphatidylcholine from egg yolk, Sigma catalog number P3556) dissolved in acetonitrile/methanol/water (80/1/19 v/v/v).

Three protocols are shown in Table 11. The solutions from each stage of the SPE protocol were analyzed using UPLC with UV detection, employing the conditions given in Tables 12 and 13. The elute solutions were neutralized by adding 35 μL of 98% formic acid before analyzing them, to avoid hydrolysis of the phosphatidylcholine (PC) catalyzed by the presence of ammonium hydroxide (NH$_4$OH). The concentrations of phosphatidylcholine in each fraction were determined by comparing the integrated peak areas to the sum of the total area.

The results (see Table 11) show that with all three protocols, most of the phosphatidylcholine (>55%) was found in the load fraction. In the 4-Step method, the 2% formic acid aqueous wash appears to result in the PC being bound on the sorbent by ion-exchange, preventing it from being effectively removed by wash 2 (methanol). As a result, a significant amount of PC is present in the elute step using 5% concentrated ammonium hydroxide in methanol. In the 3-Step method, no acidic aqueous wash was used, allowing the bulk of the remaining PC to be removed in the methanol wash step, and the remaining PC (9.1%) was removed in the elute step using 5% concentrated ammonium hydroxide in methanol. The 2-Step method did not have an aqueous or organic wash step and the bulk of the PC that was not in the load fraction was found in the elute fraction (33.8%).

TABLE 11

SPE Protocols and % Phosphatidylcholine in Each Fraction using 1 cc/30 mg Oasis MCX-NH$_4^+$ Cartridges

| Step | 4-Step | 3-Step | 2-Step |
|---|---|---|---|
| Load | 1 mL of 1 mg/mL L-α-phosphatidylcholine in acetonitrile/methanol/water 80/1/19 v/v/v | | |
| Wash 1 | 1 mL of 2% Formic Acid (aq) | No WASH Used | No WASH used |
| Wash 2 | 1 mL of methanol | 1 mL of methanol | No WASH used |
| Elute | 1 mL of methanol + 5% NH$_4$OH | | |
| Results | % Phosphatidylcholine in Each Fraction | | |
| Load | 58.3% | 57.6% | 66.2% |
| Wash 1 | 6.5% | No WASH Used | No WASH Used |
| Wash 2 | 8.7% | 33.3% | No WASH Used |
| Elute | 26.5% | 9.1% | 33.8% |

TABLE 12

Chromatographic Conditions for Phosphatidylcholine Quantification

| | |
|---|---|
| Instrument | ACQUITY UPLC System/ACQUITY I-Class System |
| Column | ACQUITY UPLC BEH C$_8$ 1.7 μm 2.1 × 50 mm |
| Column Temperature | 60° C. |
| TUV | 200 nm |
| Loop Size | 2 μL |
| Injection Type | Partial loop with needle overfill |
| Injection Volume | 1.4 μL |
| Strong Wash Solvent Volume | 150 μL |
| Weak Wash Solvent Volume | 500 μL |
| Sample Temperature | 22° C. |
| Sampling Rate: | 40 (pts/sec) |
| Mobile Phase A1: | 100% water |
| Mobile Phase B1: | 100% acetonitrile |
| Strong Needle Wash: | 0.075% Trifluoroacetic acid in 100% acetonitrile |
| Weak Needle Wash: | 10% acetonitrile/90% water v/v |
| Seal wash | 10% acetonitrile/90% water v/v |

TABLE 13

Gradient Conditions for Phosphatidylcholine Quantification

| Time (min) | Flow (mL/min) | % A1 | % B1 | Curve |
|---|---|---|---|---|
| Initial | 0.5 | 99.9 | 0.1 | Initial |
| 0.5 | 0.5 | 99.9 | 0.1 | 6 |
| 7.0 | 0.5 | 40 | 60 | 6 |

TABLE 13-continued

Gradient Conditions for Phosphatidylcholine Quantification

| Time (min) | Flow (mL/min) | % A1 | % B1 | Curve |
|---|---|---|---|---|
| 8.0 | 0.5 | 5 | 95 | 6 |
| 9.5 | 0.5 | 5 | 95 | 6 |

TABLE 13-continued

Gradient Conditions for Phosphatidylcholine Quantification

| Time (min) | Flow (mL/min) | % A1 | % B1 | Curve |
|---|---|---|---|---|
| 9.8 | 0.5 | 99.9 | 0.1 | 6 |
| 10.5 | 0.5 | 99.9 | 0.1 | 6 |

Example 6

Four batches of modified Oasis MCX (Oasis MCX-$NH_4^+$) sorbent were prepared using the conditions shown in Table 14.

The 4-Step protocol (see Table 11) was used to evaluate each batch. The solutions from each stage of the SPE protocol were analyzed using UPLC with UV detection, employing the conditions given in Tables 12 and 13. The elute solutions were neutralized by adding 35 μL of 98% formic acid before analyzing them, to avoid hydrolysis of the phosphatidylcholine (PC) catalyzed by the presence of ammonium hydroxide ($NH_4OH$). The concentrations of phosphatidylcholine in each fraction were determined by comparing the integrated peak areas to the sum of the total area.

The results (see Table 15) show that with the 4-Step protocol, the four batches of Oasis MCX-$NH_4^+$ sorbent performed equivalently. Most of the phosphatidylcholine (>80%) was found in the load fraction. Very little was found in the aqueous wash fraction (<2.5%) or methanol wash fraction (<4.5%), and ca 10-12% was found in the elute fraction. % Recovery of basic analytes on the Oasis MCX-$NH_4^+$ sorbent was determined on a single cartridge and the peak areas in the elute solution were compared to the post-spike solution to determine the % recovery. The goal of the experiment was to initially assess if the analytes are retained by the Oasis MCX-$NH_4^+$ sorbent. Recoveries of 100% or greater were achieved with the cartridges prepared using the Oasis MCX-$NH_4^+$ sorbent.

TABLE 14

Preparation Conditions for Four Batches of Oasis MCX-$NH_4^+$

| Batch ~2 grams | Batch 01 | Batch 02 | Batch 03 | Batch 04 |
|---|---|---|---|---|
| Step 1 | Pre-wash with 4% $H_3PO_4$ (aq) 100 mL/gram material; ~1 hour | NO Pre-wash | Pre-wash with 4% $H_3PO_4$ (aq) 100 mL/gram material; ~1 hour | NO Pre-wash |
| Step 2 | Filter off the fluid using a 10 μm filter | Material will be dry | Filter off the fluid using a 10 μm filter | Material will be dry |
| Step 3 | Put material in 250 mL bottle | | | |
| Step 4 | Suspend material in 100 mM Ammonium Formate, pH 3; 100 mL/gram material; ~1 hours | Suspend material in 100 mM Ammonium Formate, pH 3; 100 mL/gram material; ~1 hours | Suspend material in 100 mM Ammonium Hydroxide; 100 mL/gram material; ~1 hours | Suspend material in 100 mM Ammonium Hydroxide; 100 mL/gram material; ~1 hours |
| Step 5 | Filter off the fluid using a 10 μm filter | | | |
| Step 6 | Suspend material in 100 mM Ammonium Formate, pH 3; 100 mL/gram material; overnight | Suspend material in 100 mM Ammonium Formate, pH 3; 100 mL/gram material; overnight | Suspend material in 100 mM Ammonium Hydroxide; 100 mL/gram material; overnight | Suspend material in 100 mM Ammonium Hydroxide; 100 mL/gram material; overnight |
| Step 7 | Filter off the fluid using a 10 μm filter | | | |
| Step 8 | Wash with 100% methanol; 100 mL/gram material; pull dry and repeat | | | |
| Step 9 | Let dry in hood | | | |

TABLE 15

% Phosphatidylcholine in Each Fraction of the 4-Step SPE Protocol using Oasis MCX-$NH_4^+$ Batches

| Fraction | Batch 01 | Batch 02 | Batch 03 | Batch 04 |
|---|---|---|---|---|
| Load | 81.1 | 82.4 | 83.6 | 83.8 |
| Wash 1 | 2.4 | 2.2 | 2.5 | 2.4 |
| Wash 2 | 4.4 | 4.1 | 4.4 | 3.9 |
| Elute | 12.1 | 11.3 | 9.6 | 9.9 |
| % Recovery of Basic Analytes using Oasis MCX-$NH_4^+$ Batches 02 and 04 | | | | |
| D-Amphetamine | — | 114 | — | 112 |
| (±)-Metoprolol | — | 107 | — | 107 |
| Amitriptyline HCl | — | 115 | — | 113 |

The invention claimed is:

1. A method of performing a sample enrichment procedure, the method comprising:
adding a sample fluid that comprises at least one phospholipid and at least one target analyte to a sorbent comprising an organic copolymer that comprises a hydrophobic organic monomer, a hydrophilic organic monomer and an organic monomer comprising a cation-exchange group thereby resulting in sorbent with adsorbed phospholipid and adsorbed target analyte;
adding an aqueous solution comprising an acidic compound and a first salt species comprising an organic acid anion and an ammonium cation, wherein the first salt species is dissociated into the organic acid anion and the ammonium cation, (a) to the sample fluid prior to adding the sample fluid to the sorbent or (b) to the sorbent after adding the sample fluid to the sorbent;

adding an organic solution comprising a first organic solvent species to the sorbent thereby desorbing at least a portion of the phospholipid from the sorbent; and adding an elution solution that comprises (a) a basic compound or a second salt species, which may be the same as or different from the first salt species, and (b) a second organic solvent species, which may be the same as or different from the first organic solvent species, to the sorbent, thereby desorbing at least a portion of the target analyte from the sorbent and forming a solution of the target analyte in the elution solution.

2. The method of claim 1, wherein the target analyte is a base with a pKa of at least 5.

3. The method of claim 1, wherein the aqueous solution comprises the acidic compound in an amount sufficient to provide the aqueous solution with a pH that is at least two pH units below a lowest pKa of the target analyte.

4. The method of claim 1, wherein the acidic compound is selected from an organic acid, phosphoric acid, hydrochloric acid, or carbonic acid.

5. The method of claim 1, wherein the organic acid anion is selected from formate, acetate, propionate, butyrate, oxalate, malonate, succinate, maleate, glutarate, glycolate, lactate, malate, citrate and gluconate.

6. The method of claim 1, wherein the aqueous solution and the elution solution comprise the first salt in an amount corresponding to an ionic strength ranging from 10-250 mM.

7. The method of claim 1, wherein the first organic solvent species and the second organic solvent species are selected from methanol, ethanol, 1-propanol, 2-propanol, acetonitrile, acetone, ethyl acetate, methyl ethyl ketone, tetrahydrofuran and blends thereof.

8. The method of claim 1, wherein the elution solution comprises the basic compound in an amount sufficient to provide the elution solution with a pH that is at least two pH units above a highest pKa of the target analyte.

9. The method of claim 1, wherein the sample fluid comprises a biological sample selected from a whole blood sample, a plasma sample, a serum sample, a food sample, and a food extract sample.

10. The method of claim 1, wherein the aqueous solution comprising the acidic compound and the first salt species is added to the sample fluid prior to adding the sample fluid to the sorbent.

11. The method of claim 1, wherein the aqueous solution comprising the acidic compound and the first salt species is added to the sorbent after loading the sorbent with the sample fluid.

12. A method of performing a sample enrichment procedure, the method comprising:

adding an aqueous solution comprising an acidic compound and a first salt species comprising an organic acid anion and an ammonium cation, wherein the first salt species is dissociated into the organic acid anion and the ammonium cation, to a sample fluid that comprises at least one phospholipid and at least one target analyte, thereby forming a pretreated sample;

adding the pretreated sample to a sorbent, thereby resulting in sorbent with adsorbed phospholipid and adsorbed target analyte, wherein the sorbent comprises a hydrophobic component and a cation exchange component;

washing the sorbent in a single washing step wherein an organic solution comprising a first organic solvent species is added to the sorbent thereby desorbing at least a portion of the phospholipid from the sorbent; and adding an elution solution that comprises (a) a basic compound or a second salt species, which may be the same as or different from the first salt species, and (b) a second organic solvent species, which may be the same as or different from the first organic solvent species, to the sorbent, thereby desorbing at least a portion of the target analyte from the sorbent and forming a solution of the target analyte in the elution solution.

13. The method of claim 12, wherein the target analyte is a base with a pKa of at least 5.

14. The method of claim 12, wherein the aqueous solution comprises the acidic compound in an amount sufficient to provide the aqueous solution with a pH that is at least two pH units below a lowest pKa of the target analyte.

15. The method of claim 12, wherein the acidic compound is selected from an organic acid, phosphoric acid, hydrochloric acid, or carbonic acid.

16. The method of claim 12, wherein the sorbent comprises an organic copolymer comprising a hydrophobic organic monomer and an organic monomer comprising a cation-exchange group.

17. The method of claim 16, wherein the organic copolymer comprises a hydrophilic organic monomer.

18. A kit comprising (a) a sorbent comprising a hydrophobic moiety and a cation exchange moiety; (b) an aqueous solution comprising an acidic compound and a first salt species comprising an organic acid anion and an ammonium cation, wherein the first salt species is dissociated into the organic acid anion and the ammonium cation and (c) optionally, one or more additional components selected from any of the following: (i) a first organic solution comprising a first organic solvent species, (ii) a second organic solution that comprises (iia) a second organic solvent species, which may be the same as or different from the first organic solvent species, and (iib) a basic compound or a second salt species, which may be the same as or different from the first salt species, (ii) a collection plate or collection vials, (iv) a cap mat, (v) calibration and reference standards, (vi) identification tagging for each component, and (vii) instructions for use.

19. The kit of claim 18, wherein the sorbent comprises an organic copolymer comprising a hydrophobic organic monomer and an organic monomer comprising a cation-exchange group.

20. The kit of claim 19, wherein the organic copolymer comprises a hydrophilic organic monomer.

* * * * *